United States Patent
Schäfer et al.

(10) Patent No.: US 9,610,568 B2
(45) Date of Patent: Apr. 4, 2017

(54) CATALYTICALLY ACTIVE BODY FOR THE SYNTHESIS OF DIMETHYL ETHER FROM SYNTHESIS GAS

(71) Applicant: BASF SE, Ludwigshafen (DE)

(72) Inventors: Alexander Schäfer, Limburgerhof (DE); Thorsten von Fehren, Bürstadt (DE); Rostam Madon, Flemington, NJ (US)

(73) Assignee: BASF SE, Ludwigshafen (DE)

( * ) Notice: Subject to any disclaimer, the term of this patent is extended or adjusted under 35 U.S.C. 154(b) by 730 days.

(21) Appl. No.: 13/765,716

(22) Filed: Feb. 13, 2013

(65) Prior Publication Data

US 2013/0210940 A1    Aug. 15, 2013

Related U.S. Application Data

(60) Provisional application No. 61/598,932, filed on Feb. 15, 2012.

(51) Int. Cl.
| | |
|---|---|
| *B01J 23/80* | (2006.01) |
| *B01J 31/04* | (2006.01) |
| *B01J 27/25* | (2006.01) |
| *C07C 41/09* | (2006.01) |
| *B01J 21/04* | (2006.01) |
| *C07C 41/01* | (2006.01) |
| *B01J 23/72* | (2006.01) |

(52) U.S. Cl.
CPC .............. *B01J 23/80* (2013.01); *B01J 21/04* (2013.01); *B01J 27/25* (2013.01); *B01J 31/04* (2013.01); *C07C 41/01* (2013.01); *C07C 41/09* (2013.01); *B01J 23/72* (2013.01)

(58) Field of Classification Search
CPC ............ B01J 23/72; B01J 23/80; B01J 21/04
USPC ................... 502/345, 346, 342, 343
See application file for complete search history.

(56) References Cited

U.S. PATENT DOCUMENTS

| 4,423,155 A | 12/1983 | Bell et al. |
| 6,608,114 B1 | 8/2003 | Heydorn et al. |
| 2008/0125311 A1 | 5/2008 | Baek et al. |
| 2011/0105306 A1 | 5/2011 | Chien et al. |

FOREIGN PATENT DOCUMENTS

| CN | 1085824 | * | 4/1994 |
| CN | 1683076 A | | 10/2005 |
| CN | 101601995 A | | 12/2009 |
| JP | 2005066516 A | * | 3/2005 |
| WO | WO-2007005126 A1 | | 1/2007 |
| WO | WO-2008157682 A1 | | 12/2008 |
| WO | WO-2009007113 A1 | | 1/2009 |

OTHER PUBLICATIONS

Machine Translation JP 2005066516A.*
Kawamura, "Preparation of Cu/ZnO/Al2O3 catalyst for a micro methanol reformer", 2005, Journal of Power Sources, 150, 20-26.*
CN 1085824 (Machine Translation).*
U.S. Appl. No. 61/599,116.
U.S. Appl. No. 61/598,931.
U.S. Appl. No. 12/944,317, filed Nov. 11, 2010, Madon et al.
U.S. Appl. No. 13/219,042, filed Aug. 26, 2011, Hatscher et al.
Ertl et al., Handbook of Heterogeneous Catalysis, "Chapter 2.3.3", vol. 1, pp. 100-119 (2008).
HORIBA Scientific, A Guidebook to Particle Size Analysis, pp. 6.
Sofianos, A., et al., "Conversion of Synthesis Gas to Dimethyl Ether over Bifunctional Catalytic Systems", Ind. Eng. Chem. Res., vol. 30, No. 11, (1991), pp. 2372-2378.

* cited by examiner

*Primary Examiner* — Matthew E Hoban
*Assistant Examiner* — James Fiorito
(74) *Attorney, Agent, or Firm* — Drinker Biddle & Reath LLP; Geoffrey Zelley

(57) ABSTRACT

The invention relates to a catalytically active body for the synthesis of dimethyl ether from synthesis gas. In particular, the invention relates to an improved catalytically active body for the synthesis of dimethyl ether, whereby the components of the active body comprise a defined particle size distribution. Furthermore, the present invention concerns a method for the preparation of a catalytically active body, the use of the catalytically active body and a method for preparation of dimethyl ether from synthesis gas.

17 Claims, No Drawings

CATALYTICALLY ACTIVE BODY FOR THE SYNTHESIS OF DIMETHYL ETHER FROM SYNTHESIS GAS

CROSS-REFERENCE TO RELATED APPLICATIONS

This application claims the benefit of U.S. Provisional Application No. 61/598,932, filed Feb. 15, 2012, which is incorporated herein by reference.

FIELD OF THE INVENTION

The invention relates to a catalytically active body for the synthesis of dimethyl ether from synthesis gas. In particular, the invention relates to an improved catalytically active body for the synthesis of dimethyl ether, whereby the components of the active body comprise a defined particle size distribution. Furthermore, the present invention concerns a method for the preparation of a catalytically active body, the use of the catalytically active body and a method for preparation of dimethyl ether from synthesis gas.

BACKGROUND OF THE INVENTION

Hydrocarbons are essential in modern life and used as fuel and raw materials, including the chemical, petrochemical, plastics, and rubber industry. Fossil fuels such as oil and natural gas are composed of hydrocarbons with a specific ratio of carbon to hydrogen. In spite their wide application and high demand, fossil fuels also have limitations and disadvantages in the view of being a finite resource and their contribution to global warming if they are burned.

Research on alternative fuels was mainly started due to ecological and economical considerations. Among the alternative fuels, dimethyl ether (DME), which is recently discovered as a clean fuel, can be synthesized from synthetic gas that was generated from different primary sources. These primary sources can be natural gas, coal, heavy oil, and also from biomass. Up to now, only two DME synthesis procedures from synthesis gas have been claimed, whereby one is the traditional methanol synthesis, followed by a dehydration step and the other is a direct conversion of synthesis gas to DME in one single step.

Recently, attention has been directed towards the direct synthesis of dimethyl ether from synthesis gas, using a catalytic system that combines a methanol synthesis catalyst and a catalyst for dehydration of said alcohol. It was confirmed on the basis of experimental studies that both, the stage of methanol synthesis and the stage of methanol dehydration, could be conducted simultaneously on one appropriate catalytic system. Depending upon the applied synthesis gas the catalyst might additionally show water gas shift activity.

Most known methods of producing methanol involve synthesis gas. Synthesis gas is a mixture of mainly hydrogen, carbon monoxide and carbon dioxide, whereby Methanol is produced out of it over a catalyst.

$$CO + 2H_2 \leftrightarrow CH_3OH$$

In a following step Methanol can be converted into DME by dehydration over an acidic catalyst.

$$2CH_3OH \leftrightarrow CH_3OCH_3 + H_2O$$

In the direct DME production there are mainly two overall reactions that occur from synthesis gas. These reactions, reaction (1) and reaction (2), are listed below.

$$3CO + 3H_2 \leftrightarrow CH_3OCH_3 + CO_2 \qquad (1)$$

$$2CO + 4H_2 \leftrightarrow CH_3OCH_3 + H_2O \qquad (2)$$

Reaction (1) occurs with the combination of three reactions, which are Methanol synthesis reaction, Methanol dehydration reaction, and water gas shift reaction:

$$2CO + 4H_2 \leftrightarrow 2CH_3OH \text{ (methanol synthesis reaction)}$$

$$2CH_3OH \leftrightarrow CH_3OCH_3 + H_2O \text{ (methanol dehydration reaction)}$$

$$CO + H_2O \leftrightarrow CO_2 + H_2 \text{ (water gas shift reaction)}$$

The reaction (1) has a stoichiometric ratio $H_2/CO$ of 1:1 and has some advantages over reaction (2). For example reaction (1) generally allows higher single pass conversions and less energy-consuming in comparison to the removal of water from the system in reaction (2).

Methods for the preparation of dimethyl ether are well-known from prior art. Several methods are described in the literature where DME is produced directly in combination with methanol by the use of a catalyst active body in both the synthesis of methanol from synthesis gas and methanol dehydration. Suitable catalysts for the use in the synthesis gas conversion stage include conventionally employed methanol catalyst such as copper and/or zinc and/or chromium-based catalyst and methanol dehydration catalyst.

The document U.S. Pat. No. 6,608,114 B1 describes a process for producing DME by dehydrating the effluent stream from the methanol reactor, where the methanol reactor is a slurry bubble column reactor (SBCR), containing a methanol synthesis catalyst that converts a synthesis gas stream comprising hydrogen and carbon monoxide into an effluent stream comprising methanol.

Document WO 2008/157682 A1 provides a method of forming dimethyl ether by bimolecular dehydration of methanol produced from a mixture of hydrogen and carbon dioxide, obtained by reforming methane, water, and carbon dioxide in a ratio of about 3 to 2 to 1. Subsequent use of water produced in the dehydration of methanol in the bireforming process leads to an overall ratio of carbon dioxide to methane of about 1:3 to produce dimethyl ether.

Document WO 2009/007113 A1 describes a process for the preparation of dimethyl ether by catalytic conversion of synthesis gas to dimethyl ether comprising contacting a stream of synthesis gas, comprising carbon dioxide with one or more catalysts active in the formation of methanol and the dehydration of methanol to dimethyl ether, to form a product mixture comprising the components dimethyl ether, carbon dioxide and unconverted synthesis gas, washing the product mixture comprising carbon dioxide and unconverted synthesis gas in a first scrubbing zone with a first solvent rich in dimethyl ether and subsequently washing the effluent from the first scrubbing zone in a second scrubbing zone with a second solvent rich in methanol to form a vapor stream comprising unconverted synthesis gas stream with reduced content of carbon dioxide transferring the vapor stream comprising unconverted synthesis gas stream with reduced carbon dioxide content for the further processing to dimethyl ether.

Document WO 2007/005126 A2 describes a process for the production of synthesis gas blends, which are suitable for conversion either into oxygenates such as methanol or into Fischer-Tropsch-liquids.

The U.S. Pat. No. 6,191,175 B1 describes an improved process for the production of methanol and dimethyl ether mixture rich in DME from essentially stoichiometrically balance synthesis gas by a novel combination of synthesis steps.

In document US 2008/125311 A1 is a catalyst used for producing dimethyl ether, a method of producing the same, and a method of producing dimethyl ether using the same. More particularly, the present invention relates to a catalyst used for producing dimethyl ether comprising a methanol synthesis catalyst produced by adding one or more promoters to a main catalyst comprised of a Cu—Zn—Al metal component and a dehydration catalyst formed by mixing Aluminium Phosphate ($AlPO_4$) with gamma alumina, a method of producing the same, and a method of producing dimethyl ether using the same, wherein a ratio of the main catalyst to the promoter in the methanol synthesis catalyst in a range of 99/1 to 95/5, and a mixing ratio of the methanol synthesis catalyst to the dehydration catalyst is in a range of 60/40 to 70/30.

The processes for the preparation of dimethyl ether according to the prior art bear the drawbacks that different steps have to be undergone to get an efficient DME production. Besides this, the catalyst used in the method known in prior art does not achieve the thermodynamic possibilities. Therefore it is still desirable to increase the yield of DME in the synthesis gas conversion.

SUMMARY OF THE INVENTION

The object of the present invention is to provide a catalytically active body that shows the ability to convert CO-rich synthesis gas selectively into dimethyl ether and $CO_2$, whereby ideally the yield of the DME is increased in comparison to the state of the art. If the conversion is incomplete, the resulting off-gas comprises hydrogen and carbon monoxide preferably in the ratio $H_2/CO\sim1$. Thus the off-gas can be recycled directly after the separation of the product DME and $CO_2$. In addition, it is an object of the present invention to provide a method for the preparation of a catalytically active body and a method for the preparation of dimethyl ether from synthesis gas, comprising the inventive catalytically active body and also the use of the catalytically active body.

These objects are achieved by a catalytically active body for the synthesis of dimethyl ether from synthesis gas, comprising a mixture of:
 (A) 70-90% by weight of a methanol-active component, selected from the group consisting of copper oxide, aluminium oxide, zinc oxide, amorphous aluminium oxide, ternary oxide or mixtures thereof,
 (B) 10-30% by weight of an acid component, selected from the group consisting of aluminium hydroxide, aluminium oxide hydroxide and/or γ-aluminiumoxide with 0.1-20% by weight of Niobium, Tantalum, Phosphorus or Boron, related to component (B), or mixtures thereof,
 (C) 0-10 Gew.-% by weight of at least one additive, whereby the sum of the components (A), (B) and (C) is in total 100% by weight.

Preferably, the ternary oxide is a zinc-aluminium-spinel.

In a preferred embodiment of the catalytically active body the mixture comprises:
 (A) 70-90% by weight of a methanol-active component, selected from the group consisting of copper oxide, aluminium oxide, zinc oxide, amorphous aluminium oxide, ternary oxide or mixtures thereof, whereby the component (A) has a particle size distribution characterized by a D-10 value of 5-140 µm, a D-50 value of 40-300 µm, and a D-90 value of 180-800 µm,
 (B) 10-30% by weight of an acid component, selected from the group consisting of aluminium hydroxide, aluminium oxide hydroxide and/or γ-aluminiumoxide with 0.1-20% by weight of Niobium, Tantalum, Phosphorus or Boron, related to component (B), or mixtures thereof, whereby the component (B) has a particle size distribution characterized by a D-10 value of 5-140 µm, a D-50 value of 40-300 µm, and a D-90 value of 180-800 µm,
 (C) 0-10 Gew.-% by weight of at least one additive, whereby the sum of the components (A), (B) and (C) is in total 100% by weight and the particle size of components (A) and (B) being maintained in the catalytically active body.

This particle size distribution can be determined via state of the art analysis techniques, e.g. via analysis apparatus like Mastersizer 2000 or 3000 by Malvern Instruments GmbH. The particle size distribution in the sense of the invention is characterized by the D10-, D50-, and D-90 value. The definition of D10 is: that equivalent diameter where 10 mass % (of the particles) of the sample has a smaller diameter and hence the remaining 90% is coarser. The definition of D50 and D90 can be derived similarly (see: HORIBA Scientific, A Guidebook to Particle Size Analysis" page 6)

The inventive catalytically active body is characterized by a high turnover of carbon monoxide, preferably at 180° C. to 350° C. and particular at 200° C. to 300° C. For example, a suitable pressure for the synthesis of DME is preferably in the range from 20 to 80 bar and in particular from 30 to 50 bar.

Preferably, the components (A) or (B) have a particle size distribution characterized by a D-10, D-50, and D-90 value of 5-80 µm, 40-270 µm, and 250-800 µm respectively. In a further embodiment the particle size distribution from component (A) can be different from component (B). In particular, the components (A) or (B) have a particle size distribution characterized by a D-10, D-50, and D-90 value of 5-50 µm, 40-220 µm, and 350-800 µm respectively. In a further embodiment the particle size distribution from component (A) can be different from component (B).

In the sense of the present invention a catalytically active body can be a body known in the art that contains pores or channels or other features for enlargement of surface, which will help to bring the educts in contact that they can react to the desired product. A catalytically active body in the sense of the present invention can be understood as a physical mixture, whereby the components (A) and (B) contact each other and presenting channels and/or pores between their contact surfaces. Preferably, the components (A) and (B) are not melted or sintered at their contact surfaces.

A methanol-active component in the sense of the present invention is a component which leads to the formation of methanol, starting from hydrogen, carbon monoxide or carbon dioxide or mixtures thereof. Preferably, the methanol-active compound is a mixture of copper oxide, aluminium oxide and zinc oxide, whereby copper oxide can consist of all kinds of oxides of copper. In particular, copper has the oxidation state (I) or (II) in the oxide. The aluminium oxide according to the present invention can also be referred to γ-alumina or corundum, whereby zinc in zinc oxide in the sense of the present invention preferably has the oxidation state (II).

In a preferred embodiment of the catalytically active body, the component (B) is aluminium oxide hydroxide and γ-aluminiumoxide in a ratio of 3:7 to 6:4, preferably in a ratio of 1:2 to 5:4, whereby the ratio is by weight.

Component (B) is selected from the group consists of aluminium hydroxide, aluminium oxide hydroxide and/or γ-aluminiumoxide with 0.1-20% by weight of Niobium, Tantalum, Phosphorus or Boron, or mixtures thereof, related to component (B). Preferably, component (B) is of selected from the group consisting of aluminium hydroxide, aluminium oxide hydroxide and/or γ-aluminiumoxide with 1-10% by weight of Niobium, Tantalum, Phosphorus, or Boron, related to component (B).

In a preferred embodiment of the catalytically active body, the component (A) comprises 50-80% by weight of copper oxide, 15-35% by weight of ternary oxide and 15-35% by weight of zinc oxide and the sum of which is in total 100% by weight. In particular the component (A) comprises 65-75% by weight of copper oxide, 20-30% by weight of ternary oxide and 20-30% by weight of zinc oxide and the sum of which is in total 100 by weight.

In a preferred embodiment of the catalytically active body, the component (A) comprises 50-80% by weight of copper oxide, 2-8% by weight of boehmite and 15-35% by weight of zinc oxide and the sum of which is in total 100% by weight. In particular the component (A) comprises 65-75% by weight of copper oxide, 3-6% by weight of boehmite and 20-30% by weight of zinc oxide and the sum of which is in total 100% by weight.

In a preferred embodiment of the catalytically active body, the component (A) comprises 50-80% by weight of copper oxide, 2-8% by weight of amorphous aluminium oxide and 15-35% by weight of zinc oxide and the sum of which is in total 100% by weight. In particular the component (A) comprises 65-75% by weight of copper oxide, 3-6% by weight of amorphous aluminium oxide and 20-30% by weight of zinc oxide and the sum of which is in total 100% by weight.

In a preferred embodiment of the catalytically active body, the component (A) comprises 50-80% by weight of copper oxide, 2-8% by weight of aluminium oxide and 15-35% by weight of zinc oxide and the sum of which is in total 100% by weight. In particular the component (A) comprises 65-75% by weight of copper oxide, 3-6% by weight of aluminium oxide and 20-30% by weight of zinc oxide and the sum of which is in total 100% by weight.

In a preferred embodiment of the catalytically active body, component (B) has a surface area from 70-270 $m^2/g$ with a pore volume in the range from 0.35-0.1.45 ml/g, preferably a surface area from 85-220 $m^2/g$ with a pore volume in the range from 0.35-1.35 ml/g and in particular a surface area from 110-200 $m^2/g$ with a pore volume in the range from 0.51-1.14 ml/g.

In a preferred embodiment of the catalytically active body component (B) is boehmite, preferably a boehmite containing mineral. Boehmite occurs in tropical laterites and bauxites developed on alumino-silicate bedrock. It also occurs as a hydrothermal alteration product of corundum and nepheline. It occurs with kaolinite, gibbsite and diaspore in bauxite deposits and with nepheline, gibbsite, diaspore, natrolite and analcime in nepheline pegmatites.

In the sense of the present invention an additive (C) can be a structure-promoter like but not limited a thermally decomposable compound like polymers, wood dust, flour, graphite, film material, a painting, straw, strearic acid, palmitic acid, celluloses or a combination thereof. For example, the structure-promotor can help to build up pores or channels.

In a preferred embodiment the catalytically active body is a pellet with a size in the range from 1×1 mm to 10×10 mm, preferably in the range from 2×2 mm to 7×7 mm. The pellet is obtained by pressing the mixture of the components (A), (B) and (C) to a pellet. In the sense of the present invention a pellet can be obtained by pressing the components (A), (B) and optionally (C) under force to the pellet, whereby the shape of the pellet can be ring-shaped, star-shaped or spherical-shaped. Furthermore the pellet can be hollow strings, triloops, multihole pellets, extrudates and alike.

The present invention further relates to a method for the preparation of a catalytically active body, comprising the step:
  d) preparing a physical mixture comprising:
    (A) 70-90% by weight of a methanol-active component, selected from the group consisting of copper oxide, aluminium oxide, zinc oxide, amorphous aluminium oxide, ternary oxide or mixtures thereof,
    (B) 10-30% by weight of an acid component, selected from the group consisting of aluminium hydroxide, aluminium oxide hydroxide and/or γ-aluminiumoxide with 0.1-20% by weight of Niobium, Tantalum, Phosphorus or Boron, related to component (B), or mixtures thereof,
    (C) 0-10 Gew.-% by weight of at least one additive, whereby the sum of the components (A), (B) and (C) is in total 100% by weight.

In this context, the meanings of the features are the same as for the catalytically active body already mentioned.

In the sense of the present invention preparing a physical mixture means that the different compounds (A), (B) and (C) are brought in contact without further chemical modification.

In a preferred embodiment of the method, the component (A) has a particle size distribution characterized by a D-10 value of 5-80 μm, a D-50 value of 40-270 μm, and a D-90 value of 250-800 μm, whereby the component (B) has a particle size distribution characterized by a 0-10 value of 5-80 μm, a D-50 value of 40-270 μm, and a D-90 value of 250-800 μm and the particle size distribution of components (A) and (B) being maintained in the catalytically active body. In a particular embodiment of the method, the component (A) has a particle size distribution characterized by a D-10 value of 5-50 μm, a D-50 value of 40-220 μm, and a D-90 value of 350-800 μm, whereby the component (B) has a particle size distribution characterized by a D-10 value of 5-50 μm, a D-50 value of 40-220 μm, and a D-90 value of 350-800 μm and the particle size distribution of components (A) and (B) being maintained in the catalytically active body.

In a preferred embodiment the method comprising further the steps:
  a) precipitation a copper-, zinc- or aluminium salt or a mixture thereof,
  b) calcination of the product obtained in step a),
  c) calcination of a salt comprising Niobium, Tantalum, Phosphorus or Boron with a mixture of aluminium hydroxide, aluminium oxide hydroxide and/or γ-aluminiumoxide Preferably the steps a), b) and c) are carried out before the step d). Preferably, in step c) the salt further comprises oxalate, acetate and acetylacetonate.

Preferably, the obtained product consists after step d) of 70-90% by weight of a methanol-active component (A), selected from the group consisting of copper oxide, aluminium oxide and zinc oxide or mixtures thereof, 10-30% by weight of an acid component (B), selected from the group consists of aluminium hydroxide, aluminium oxide hydroxide and/or γ-aluminiumoxide with 0.1-20% by weight of Niobium, Tantalum, Phosphorus or Boron, related to component (B), or mixtures thereof. Preferably, after step d) the component (A) has a particle size distribution characterized by a D-10 value of 5-140 μm, a D-50 value of 40-300 μm, and a D-90 value of 180-800 μm and the component (B) has a particle size distribution characterized by a D-10 value of 5-140 μm, a D-50 value of 40-300 μm, and a D-90 value of 180-800 μm.

Preferably, the method comprises at least spray drying, filtration, grinding, sieving or further steps, known in the art to create a catalytically active body, or combinations thereof.

In the sense of the present invention precipitation is a method for the formation of a solid in a solution or inside another solid during a chemical reaction or by diffusion in a solid. The precipitation techniques are known in the art, see also Ertl, Gerhard, Knözinger, Helmut, Schüth, Ferdi, Weitkamp, Jens (Hrsg.) "Handbook of Heterogeneous Catalysis" 2nd edition 2008, Wiley VCH Weinheim, Vol. 1, chapter 2. For example salts of copper, zinc or aluminium are dissolved in a solvent, in particular water. At least two of the salts of either copper, zinc, or aluminium can be dissolved in a solvent, heated and a basic solution can be prepared and added. Both solutions can be added in parallel to the template, till the salt-solution is consumed. After this the suspension is vacuumed, dried, and calcinated under air flow.

Preferred anions in the salts for copper, zinc, or aluminium are selected from the group consisting of, nitrate, acetate, carbonate, halide, nitrite, sulfate, sulfite, sulfide, phosphate ion or silicate. In particular, salts of copper, zinc or aluminium formed with the above mentioned anions can be converted into oxides of copper, zinc or aluminium applying a calcination step.

Calcination in the sense of the present invention can be understood as a thermal treatment process applied to ores and other solid materials to bring about a thermal decomposition, phase transition, or removal of a volatile fraction. The calcination process normally takes place at temperatures below the melting point of the product materials. Mostly it is done under oxygen-containing atmosphere. In some cases the calcination can be performed under inert atmosphere (e.g. nitrogen).

In the sense of the present invention preparing a physical mixture means that the different compounds (A), (B) and (C) are bringing in contact without further chemical modification.

In particular the components (A), (B) and (C) can be compacted in a presser, a squeezer, a crusher or a squeezing machine, preferably after step a), b), c) or d). Compacting in the sense of the present invention can mean that particles of a defined particle size distribution are pressed to bodies, which have a diameter in the range of 1 to 10 mm and a height of 1 to 10 mm. Preferably the particle size distribution is still left after the compacting.

In a preferred embodiment of the method a pellet is formed, preferably with a size in the range from 1×1 mm to 10×10 mm, especially in the range from 2×2 mm to 7×7 mm.

In a preferred embodiment of the method, the components (A) and (B) independently pressed through at least one sieve, whereby the sieve exhibits a mesh size from 0.005 to 5 mm in order to obtain a particle size distribution characterized by a D-10 value of 5-140 μm, a D-50 value of 40-300 μm, and a D-90 value of 180-800 μm. Preferably the sieve exhibits a mesh size from 0.005 to 1.50 mm and in particular a mesh size from 0.005 to 0.8 mm. In particular the particles can also exhibit particle size distribution characterized by a D-10, D-50, and D-90 value of 5-140 μm, 40-300 μm, and 180-800 μm respectively. Thereby the components (A) and (B) can be obtained as particles with a defined particle size distribution, also referred in the sense of the present invention as a split-fraction. Because of this split-fraction the CO-conversion increases when synthesis gas contacts the split-fraction. Furthermore the yield of the DME increases, when synthesis gas is converted to DME by the catalytically active body. Preferably, this step is included in step d).

In a further embodiment component (C) is admixed to the components (A) and (B) before sieving.

In a preferred embodiment of the preparation of a catalytically active body at least three different sieves are used, whereby the components (A) and (B) are pressed in direction from the sieve with the biggest mesh size to the sieve with the smallest mesh size.

By using three sieves with different mesh sizes the components (A) and (B) are initially pressed into the sieve with the biggest mesh size, which results in particles with the maximal size of the mesh size of this sieve. Preferably, the particle size distribution of the components (A) and (B) is characterized by a D-10 value of 5-140 μm, a D-50 value of 40-300 μm, and a D-90 value of 180-800 μm. These particles can also be broken during the first sieving, so that smaller particles are obtained, which can go through the second sieve, which exhibits a smaller mesh size. Therefore a first fraction with a particle size distribution can be obtained before the second sieve. This fraction can also be used as a catalytically active body. Besides this, the particles which go through the second sieve with a mesh size smaller than the first sieve, but bigger than the third sieve, can be obtained behind the second sieve and before the smallest sieve with the smallest mesh size. Also here the particles obtained after the second (middle) sieve can be used as a catalytically active body. In addition to this, the particles obtained after the sieve with the biggest mesh size could be pressed through the second sieve in order to reduce the particle size.

In a preferred embodiment of the method according to the present invention in step a) at least a part of the component (A) is prepared by precipitation reaction and/or calcination. In the sense of the present invention precursors of the component (A) in form of a salt in a solution can be heated and adjusted to a defined pH-value. After this, a calcination step can be carried out, whereby calcination is known from prior art. These steps can lead to the desired component (A).

In a preferred embodiment of the method at least one part of component (A) is precipitated and whereby at least another part of component (A), which is not subjected to the first precipitation, is added to the precipitate. Preferably, it is added by spray drying or precipation.

In a preferred embodiment the method further comprises the step e) adding a mixture of hydrogen and nitrogen to component (A) and/or (B). Preferably the content of the volume of the hydrogen is less than 5% in the mixture.

The present invention further relates to a method for the preparation of dimethyl ether from synthesis gas comprising at least the steps:
f) reducing the catalytically active body
g) contacting the catalytically active body in a reduced form with hydrogen and at least one of carbon monoxide or carbon dioxide.

In a further embodiment the method comprising the steps:
h) providing the inventive catalytically active body, in particular in form of pellets
i) filling the catalytically active body in a reactor, j) reducing the catalytically active body at a temperature between 140° C. and 240° C. with at least a nitrogen and hydrogen mixture.

The present invention further relates to the use of a catalytically active body according to the present invention for the preparation of dimethyl ether. Preferred admixtures and preferred methods for the preparation a mentioned above and also included in the use.

The present invention is further illustrated by the following examples:

A) SYNTHESIS OF THE METHANOL-ACTIVE COMPOUNDS

1. Example

Two solutions are prepared for the precipitation of the components:
Solution 1:
A solution of 1.33 kg copper nitrate, 2.1 kg zinc nitrate and 0.278 kg aluminium nitrate are solved in 15 L water.
Solution 2:
2.344 kg sodium bicarbonate is dissolved in 15 L water.
Both solutions are separately heated to 90° C., followed by the fast addition of solution 1 to solution 2 within 1-2 minutes under stirring. Afterwards 15 min is stirred and the precipitation is filtered and washed with water till it is free of nitrates. The filter cake is dried at 110° C. and is calcinated for 4 h at 270° C. under nitrogen atmosphere. The metal content of the catalyst is in atom-%: Cu 38.8; Zn 48.8 and Al 12.9.

2. Example

Two solutions are prepared for the precipitation of the components:
Solution 1:
A solution of 2.66 kg copper nitrate, 1.05 kg zinc nitrate and 0.278 kg aluminium nitrate are solved in 15 L water.
Solution 2:
2.344 kg sodium bicarbonate is dissolved in 15 L water.
The same procedure as described in the 1. Example, whereby the metal content of the catalyst is in atom %: Cu 61.6; Zn 28.1 and Al 10.9.

3. Example

Preparation of Me30 i. Precipitation:
A sodium bicarbonate solution (20%) is prepared, whereby 11 kg sodium bicarbonate is dissolved in 44 kg demineralised water. Also a Zn/Al-solution is prepared consisting of 6.88 kg zinc nitrate and 5.67 kg aluminium nitrate and 23.04 kg water. Both solutions are heated to 70° C. A template filled with 12.1 L demineralised water is also heated to 70° C. Both solutions are added in parallel to the template at a pH=7, till the Zn/Al-solution is consumed. Afterwards 15 h is stirred at a pH=7. After this the suspension is vacuumed and washed to a content of sodium oxide <0.10% and the water is free of nitrate. The product is dried for 24 h at 120° C. and calcinated for 1 h at 350° C. under air flow.
ii. Precipitation:
A sodium bicarbonate solution (20%) is prepared, whereby 25 kg sodium bicarbonate is dissolved in 100 kg demineralised water. Also a Cu/Zn-nitrate solution is prepared consisting of 26.87 kg copper nitrate and 5.43 kg zinc nitrate and 39 kg water. Both solutions are heated to 70° C. After the Cu/Zn-nitrate solution has reached a temperature of 70° C., the product of the 1.precipitation is added slowly and the pH-value is adjusted to pH=2. Also a solution of nitric acid (65%) is provided (650 g conc. $HNO_3$ and 350 g demineralised water). A template filled with 40.8 L demineralised water is also heated to 70° C. Both solutions (sodium bicarbonate and Cu/Zn-nitrate solution) are added in parallel to the template at a pH=6.7, till the Cu/Zn-nitrate solution is consumed. Afterwards 10 h is stirred whereby the pH-value is adjusted to pH=6.7 with the nitric acid (65%). After this the suspension is vacuumed and washed to a content of sodium oxide <0.10% and the water is free of nitrate. The product is dried for 72 h at 120° C. and calcinated for 3 h at 300° C. under air flow. After cooling to room temperature the material is ready for use.

B) SYNTHESIS OF ACID COMPOUNDS

Synthesis of an $Al_2O_3$/AlOOH-Mixture Doped with Niobium (0.255% by Weight)

An impregnated solution is prepared that consists of 0.5 g ammonium niobate(V) oxalate and 27.4 ml demineralised water. With spray-watering this solution is applied onto 40 g $Al_2O_3$/AlOOH-mixture (crushed extrudates consisting of 60% gamma-$Al_2O_3$ and 40% boehmite). Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

Synthesis of an $Al_2O_3$/AlOOH-Mixture Doped with Niobium (1.02% by Weight)

An impregnated solution is prepared that consists of 2 g ammonium niobate(V) oxalate and 27.4 ml demineralised water. With spray-watering this solution is applied onto 40 g $Al_2O_3$/AlOOH-mixture (crushed extrudates consisting of 60% gamma-$Al_2O_3$ and 40% boehmite). Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

Synthesis of an $Al_2O_3$/AlOOH-Mixture Doped with Niobium (2.04% by Weight)

An impregnated solution is prepared that consists of 4 g ammonium niobate(V) oxalate and 27.4 ml demineralised water. With spray-watering this solution is applied onto 40 g $Al_2O_3$/AlOOH-mixture (crushed extrudates consisting of 60% gamma-$Al_2O_3$ and 40% boehmite). Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

Synthesis of an $Al_2O_3$/AlOOH-Mixture Doped with Niobium (3.06% by Weight)

An impregnated solution is prepared that consists of 6 g ammonium niobate(V) oxalate and 27.4 ml demineralised water. With spray-watering this solution is applied onto 40 g $Al_2O_3$/AlOOH-mixture (crushed extrudates consisting of 60% gamma-$Al_2O_3$ and 40% boehmite). Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

Synthesis of an $Al_2O_3$/AlOOH-Mixture Doped with Niobium (8.16% by Weight)

An impregnated solution is prepared that consists of 16 g ammonium niobate(V) oxalate dissolved in 100 ml water. An 40 g $Al_2O_3$/AlOOH-mixture (crushed extrudates consisting of 60% gamma-$Al_2O_3$ and 40% boehmite) is added in portions under stirring and afterwards 10 min stirred. In the following step the suspension is exhausted by a Nutsche Filter. Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

Synthesis of an $Al_2O_3$/AlOOH-Mixture Doped with Samarium (2.04% by Weight)

An impregnated solution is prepared that consists of 2.61 g samarium(III)-acetate hydrate and 27.4 ml demineralised water. With spray-watering this solution is applied onto 40 g $Al_2O_3$/AlOOH-mixture (crushed extrudates consisting of 60% gamma-$Al_2O_3$ and 40% boehmite). Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room tem

Synthesis of an $Al_2O_3$/AlOOH-Mixture Doped with Tin (2.04% by Weight)

An impregnated solution is prepared that consists of 2.39 g tin(II)-acetate and 27.4 ml demineralised water. With spray-watering this solution is applied onto 40 g $Al_2O_3$/AlOOH-mixture (crushed extrudates consisting of 60% gamma-$Al_2O_3$ and 40% boehmite). Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

Synthesis of an $Al_2O_3$/AlOOH-Mixture Doped with Tungsten (2.04% by Weight)

An impregnated solution is prepared that consists of 1.25 g ammonium metatungstate hydrate and 27.4 ml demineralised water. With spray-watering this solution is applied onto 40 g $Al_2O_3$/AlOOH-mixture (crushed extrudates consisting of 60% gamma-$Al_2O_3$ and 40% boehmite). Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

Synthesis of an $Al_2O_3$/AlOOH-Mixture Doped with Yttrium (2.04% by Weight)

An impregnated solution is prepared that consists of 3.59 g yttrium(III) acetate hydrate and 27.4 ml demineralised water. With spray-watering this solution is applied onto 40 g $Al_2O_3$/AlOOH-mixture (crushed extrudates consisting of 60% gamma-$Al_2O_3$ and 40% boehmite). Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

Synthesis of an $Al_2O_3$/AlOOH-Mixture Doped with Cerium (2.04% by Weight)

An impregnated solution is prepared that consists of 2.72 g cerium(III) acetate hydrate and 27.4 ml demineralised water. With spray-watering this solution is applied onto 40 g $Al_2O_3$/AlOOH-mixture (crushed extrudates consisting of 60% gamma-$Al_2O_3$ and 40% boehmite). Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

Synthesis of an $Al_2O_3$/AlOOH-Mixture Doped with Boron (2.04% by Weight)

An impregnated solution is prepared that consists of 6.86 g boric acid and 27.4 ml demineralised water. With spray-watering this solution is applied onto 40 g $Al_2O_3$/AlOOH-mixture (crushed extrudates consisting of 60% gamma-$Al_2O_3$ and 40% boehmite). Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

Synthesis of an $Al_2O_3$/AlOOH-Mixture Doped with Gallium (2.04% by Weight)

An impregnated solution is prepared that consists of 6.32 g gallium(III) acetylacetonat and 27.4 ml demineralised water. With spray-watering this solution is applied onto 40 g $Al_2O_3$/AlOOH-mixture (crushed extrudates consisting of 60% gamma-$Al_2O_3$ and 40% boehmite). Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

Synthesis of Boehmite Doped with Niobium (2.04% by Weight on Plural SCF 55)

An impregnated solution is prepared that consists of 4.00 g ammonium niobate(V) oxalate and 20.9 ml demineralised water. With spray-watering this solution is applied onto 40 g Plural SCF 55. Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

Synthesis of $Al_2O_3$ Doped with Niobium (2.04% by Weight on Pluralox SCF A230)

An impregnated solution is prepared that consists of 4.00 g ammonium niobate(V) oxalate and 25.6 ml demineralised water. With spray-watering this solution is applied onto 40 g Pluralox SCF A230. Afterwards this material is dried for 12 h and 90° C. in the drying oven. After drying the material is calcinated in a rotating tube for 3 h at 450° C. under nitrogen atmosphere (30 nl/h). The heating rate is 5° C./min. After cooling to room temperature the material is ready for use.

C) PREPARATION OF THE FINAL CATALYTICALLY ACTIVE BODY

The methanol-active compound and the acid compound are compacted separately in a tablet press and/or pelletizing machine. The obtained molding (diameter=ca, 25 mm, height=ca, 2 mm), is squeezed through sieves with an appropriate mesh size, so that the desired split fraction is obtained. From both fractions the proper quantity is weight in (9/1, 8/2, or 7/3 methanol-active/acidic compound) and mixed in a mixing machine (Heidolph Reax 2 or Reax 20/12). If required the compound C is added in advance.

D) TESTING CONDITIONS FOR NON-PELLETIZED MIXTURES

The catalytically active body (5 cm$^3$ by volume) is incorporated in a tubular reactor (inner diameter 0.4 cm, bedded in a metal heating body) on a catalyst bed support consisting of alumina powder as layer of inert material and is pressure-less reduced with a mixture of 1 Vol.-% $H_2$ and 99 Vol.-% $N_2$. The temperature is increased in intervals of 8 h from 150° C. to 170° C. and from 170° C. to 190° C. and finally to 230° C. At a temperature of 230° C. the synthesis gas is introduced and heated within 2 h up to 250° C. The synthesis gas consists of 45% $H_2$ and 45% CO and 10% inert gas (argon). The catalytically active body is run at an input temperature of 250° C., GHSV of 2400 h$^{-1}$ and a pressure of 50 bar.

E) TESTING CONDITIONS FOR PELLETIZED MIXTURES

Tests for pelletized materials are conducted in a similar test rick compared to the setup described above for non-pelletized materials using the same routine. Only no_tubular reactor with an inner diameter of 0.4 cm is used but a tubular reactor having an inner diameter of 3 cm. Tests for pelletized materials are done with a catalyst volume of 100 cm$^3$.
Results:
According to table 1 the different mixtures are listed.
Methanol-Active Component:
Me30: Consists of 70% by weight of CuO, 5.5% by weight $Al_2O_3$ and 24.5% by weight of ZnO.
In the following table 1 the results are presented. Me30 and D10-21 (mixture from boehmite and gamma-Alox in a ratio of 4:6), Pluralox and Plural are used.
The compositions of the catalytically active body (the corresponding D-10, D-50, and D-90 values of Me30 and of the acid component are presented in table 2) show different CO-conversions. The comparison experiments C1 to C9 showing a lower turnover, whereby the inventive experiments V1 to V9 showing an increased value.

TABLE 1

| Nr. | Mixture Me30: (Z = acide component) | Z: (doped)acid component | CO-conversion [%] | S(MeOH) | S(DME) | S(CO$_2$) | S(Others) |
|---|---|---|---|---|---|---|---|
| C1 | Me30:Z (4:1) | D10-21 (Mixture from Boehmite and gamma-Alox (40:60)) | 49.00 | 32.42 | 30.96 | 35.72 | 0.90 |
| C2 | Me30:gamma Alox (4:1) | Puralox (gamma Alox) | 59.60 | 9.09 | 45.30 | 45.36 | 0.24 |
| C3 | Me30:Boehmit (4:1) | Pural (Boemit) | 12.56 | 97.00 | 0.47 | 0.00 | 2.53 |
| V1 | Me30:Z (4:1) | Ammonium niobate(V) oxalate on D10-21 (0.255 Gew % Nb) | 82.86 | 4.37 | 47.86 | 47.43 | 0.34 |
| V2 | Me30:Z (4:1) | Ammonium niobate(V) oxalate on D10-21 (1.02% by weight Nb) | 78.54 | 7.14 | 46.03 | 46.61 | 0.22 |
| V3 | Me30:Z (4:1) | Ammonium niobate(V) oxalate on D10-21 (2.04% by weight Nb) | 81.44 | 2.62 | 48.25 | 49.06 | 0.06 |
| V4 | Me30:Z (4:1) | Ammonium niobate(V) oxalate on D10-21 (3.06% by weight Nb) | 81.20 | 6.50 | 46.24 | 46.95 | 0.32 |
| V5 | Me30:Z (4:1) | Ammonium niobate(V) oxalate on D10-21 (8.16% by weight Nb) | 82.91 | 4.42 | 47.47 | 47.68 | 0.44 |
| C4 | Me30:Z (4:1) | Samarium(III) acetat hydrate on D10-21 (2.04% by weight Sm) | 67.86 | 21.16 | 38.65 | 39.74 | 0.45 |
| C5 | Me30:Z (4:1) | Tin(II) acetat on D10-21 (2.04% by weight Sn) | 67.86 | 15.53 | 41.81 | 42.29 | 0.38 |
| C6 | Me30:Z (4:1) | Ammonium metatungstate hydrate on D10-21 (2.04% by weight W) | 67.80 | 17.74 | 40.81 | 41.02 | 0.43 |
| C7 | Me30:Z (4:1) | Yttrium(III) acetate hydrate on D10-21 (2.04% by weight Y) | 59.66 | 28.27 | 34.28 | 36.68 | 0.77 |
| C8 | Me30:Z (4:1) | Cerium(III) acetate hydrate on D10-21 (2.04% by weight Ce) | 53.67 | 30.58 | 33.30 | 35.38 | 0.74 |
| V6 | Me30:Z (4:1) | Boric acid D10-21 (2.04% by weight B) | 82.14 | 4.33 | 48.45 | 46.86 | 0.35 |
| C9 | Me30:Z (4:1) | Gallium(III)acetylacetonate on D10-21 (2.04% by weight Ga) | 41.62 | 4.94 | 49.41 | 45.22 | 0.44 |
| V7 | Me30:Z (4:1) | Tantal(V)nitrat on D10-21 (2.04% by weight Ta) | 77.59 | 3.57 | 49.57 | 46.49 | 0.37 |
| V8 | Me30:Z (4:1) | Ammonium niobate(V) oxalate on Pural (2.04% by weight Nb) | 79.11 | 6.61 | 46.68 | 46.34 | 0.36 |
| V9 | Me30:Z (4:1) | Ammonium niobate(V) oxalate on Puralox (2.04% by weight Nb) | 79.03 | 5.53 | 47.48 | 46.80 | 0.19 |

All gaseous streams were analyzed via online-GC. Argon was used as internal standard to correlate in and off gas streams.
CO conversion is given as follows: $(CO_{in} - (CO_{out} * Argon_{in}/Argon_{out}))/CO_{in} * 100\%$
S(MeOH) = Volume (MeOH) in product stream/Volume (MeOH + DME + CO$_2$ + Others without hydrogen and CO) in product stream * 100%
S(DME) = Volume (DME) in product stream/Volume (MeOH + DME + CO$_2$ + Others without hydrogen and CO) in product stream * 100%
S(CO$_2$) = Volume (CO$_2$) in product stream/Volume (MeOH + DME + CO$_2$ + Others without hydrogen and CO) in product stream * 100%
S(Others) = Volume (Others) in product stream/Volume (MeOH + DME + CO$_2$ + Others without hydrogen and CO) in product stream * 100%
"Others" are compounds that are formed out of H$_2$ and CO in the reactor that are not MeOH, DME, or CO$_2$.

TABLE 2

|  | D-10 [μm] | D-50 [μm] | D-90 [μm] |
| --- | --- | --- | --- |
| Me30 | 5.42 | 46.57 | 189.14 |
| D10-21 (Mixture from Boehmite and gamma-Alox) | 7.53 | 114.87 | 189.23 |
| Puralox (gamma Alox) | 5.06 | 57.96 | 396.86 |
| Pural (Boehmite) | 6.33 | 79.13 | 243.57 |
| Ammonium niobate(V) oxalate on D10-21 (0.255 Gew % Nb) | 11.51 | 65.55 | 217.44 |
| Boric acid D10-21 (2.04 Gew % B) | 8.49 | 98.36 | 197.83 |
| Tantal(V)nitrat on D10-21 (2.04 Gew % Ta) | 13.98 | 131.69 | 345.25 |

The invention claimed is:

1. Catalytically active body for the synthesis of dimethyl ether from synthesis gas, comprising a mixture of:
   (A) 70-90% by weight of a methanol-active component, selected from the group consisting of copper oxide, aluminium oxide, zinc oxide, amorphous aluminium oxide, ternary oxide or mixtures thereof,
   (B) 10-30% by weight of an acid component, selected from the group consisting of aluminium hydroxide, aluminium oxide hydroxide, γ-aluminiumoxide, and combinations thereof, with 0.1-20% by weight of Niobium, Tantalum, or Boron, related to component (B), or mixtures thereof,
   (C) 0-10% by weight of at least one additive, whereby the sum of the components (A), (B) and (C) is in total 100% by weight;
   wherein the component (A) has a particle size distribution characterized by a D-10 value of 5-140 μm, a D-50 value of 40-300 μm, and a D-90 value of 180-800 μm, whereby the component (B) has a particle size distribution characterized by a D-10 value of 5-140 μm, a D-50 value of 40-300 μm, and a D-90 value of 180-800 μm and the article size distribution of components (A) and (B) being maintained in the catalytically active body.

2. Catalytically active body according to claim 1, wherein component (B) is aluminium oxide hydroxide and γ-aluminiumoxide in a ratio of 3:7 to 6:4.

3. Catalytically active body according to claim 1, characterized in that component (A) comprises 50-80% by weight of copper oxide, 15-35% by weight of ternary oxide and 15-35% by weight of zinc oxide and the sum of which is in total 100% by weight.

4. Catalytically active body according to claim 1, characterized in that component (A) comprises 50-80% by weight of copper oxide, 2-8% by weight of amorphous aluminium oxide and 15-35% by weight of zinc oxide and the sum of which is in total 100% by weight.

5. Catalytically active body according to claim 1, wherein component (A) comprises 50-80% by weight of copper oxide, 2-8% by weight of aluminium oxide and 15-35% by weight of zinc oxide and the sum of which is in total 100% by weight.

6. Catalytically active body according to claim 1, wherein component (B) has a surface area from 70-270 m$^2$/g with a pore volume in the range from 0.35-1.45 ml/g.

7. Catalytically active body according to claim 1, wherein component (B) comprises boehmite.

8. Catalytically active body according to claim 1, wherein the catalytically active body is a pellet with a size in the range from 1×1 mm to 10×10 mm.

9. Method for the preparation of a catalytically active body, comprising the step:
   d) preparing a physical mixture comprising:
   (A) 70-90% by weight of a methanol-active component, selected from the group consisting of copper oxide, aluminium oxide, zinc oxide, amorphous aluminium oxide, ternary oxide or mixtures thereof,
   (B) 10-30% by weight of an acid component, selected from the group consisting of aluminium hydroxide, aluminium oxide hydroxide and/or γ-aluminiumoxide with 0.1-20% by weight of Niobium, Tantalum, Phosphorus or Boron, related to component (B), or mixtures thereof,
   (C) 0-10 Gew.-% by weight of at least one additive, whereby the sum of the components (A), (B) and (C) is in total 100% by weight; wherein the component (A) has a particle size distribution characterized by a D-10 value of 5-140 μm, a D-50 value of 40-300 μm, and a D-90 value of 180-800 μm, whereby the component (B) has a particle size distribution characterized by a D-10 value of 5-140 μm, a D-50 value of 40-300 μm, and a D-90 value of 180-800 μm and the particle size distribution of components (A) and (B) being maintained in the catalytically active body.

10. Method for the preparation of a catalytically active body according to claim 9, further comprising:
    a) precipitation of a salt of copper, zinc or aluminum or a mixture thereof,
    b) calcination of the product obtained in step a),
    c) calcination of a salt comprising Niobium, Tantalum, Phosphorus or Boron with a mixture of aluminium hydroxide, aluminium oxide hydroxide and/or γ-aluminiumoxide.

11. Method for the preparation of a catalytically active body according to claim 9, wherein a pellet is formed.

12. Method for the preparation of a catalytically active body according to claim 9, wherein the components (A) and (B) are independently pressed through at least one sieve, whereby the sieve exhibits a mesh size from 0.005 to 5 mm in order to obtain a particle size distribution characterized by a D-10 value of 5-140 μm, a D-50 value of 40-300 μm, and a D-90 value of 180-800 μm.

13. Method for the preparation of a catalytically active body according to claim 9, wherein at least three different sieves are used, whereby the components (A) and (B) are pressed in direction from the sieve with the biggest mesh size to the sieve with the smallest mesh size.

14. Method for the preparation of a catalytically active body according to claim 9, wherein in step a) at least a part of the component (A) is prepared by precipitation reaction and/or calcination.

15. Method for the preparation of a catalytically active body according to claim 9, whereby at least one part of component (A) is precipitated and whereby at least another part of component (A), which is not subjected to the first precipitation, is added to the precipitate.

16. Method for the preparation of a catalytically active body according to claim 9, wherein the method further comprises adding a mixture of hydrogen and nitrogen to component (A) and/or (B).

17. Method for the preparation of dimethyl ether from synthesis gas comprising:
    f) reducing the catalytically active body according to claim 1; and
    g) contacting the catalytically active body in a reduced form with hydrogen and at least one of carbon monoxide or carbon dioxide.

* * * * *